(12) United States Patent
Meisberger

(10) Patent No.: US 6,212,936 B1
(45) Date of Patent: Apr. 10, 2001

(54) ULTRASONIC TRANSMITTER PARTICULARLY FOR AN AIR BUBBLE DETECTOR

(75) Inventor: Artur Meisberger, St. Wendel (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/145,057

(22) Filed: Sep. 1, 1998

(30) Foreign Application Priority Data

Sep. 1, 1997 (DE) ............................................... 197 38 146

(51) Int. Cl.[7] .................................................... G01N 29/04
(52) U.S. Cl. ........................ 73/19.03; 76/632; 76/866.5
(58) Field of Search ................................. 73/19.1, 19.03, 73/54.15, 61.41, 61.49, 61.75, 64.53, 602, 620, 627, 628, 629, 630, 632, 866.5

(56) References Cited

U.S. PATENT DOCUMENTS

| 3,520,186 | 7/1970 | Adams et al. ................. 73/290 V |
| 3,710,621 | * 1/1973 | Asada ........................... 73/194 |
| 3,727,454 | * 4/1973 | Courty .......................... 73/194 |
| 3,836,949 | * 9/1974 | Ergon ............................ 340/3 |
| 3,974,681 | * 8/1976 | Namery ....................... 73/67.5 R |
| 4,130,010 | * 12/1978 | Wonn ............................ 73/19 |
| 4,138,879 | * 2/1979 | Liebermann ..................... 73/19 |
| 4,388,708 | * 6/1983 | Skrgatic et al. .................. 367/2 |
| 4,542,644 | * 9/1985 | Claytor et al. .................. 73/61 R |
| 4,736,192 | * 4/1988 | Angerer ........................ 340/384 |
| 5,583,280 | 12/1996 | Mo et al. ..................... 73/19.03 |

FOREIGN PATENT DOCUMENTS

| 33 28 907 | 2/1985 | (DE) . |
| 0 084 458 | 7/1983 | (EP) . |
| 0 340 470 | 11/1989 | (EP) . |
| 0 416 911 | 3/1991 | (EP) . |

OTHER PUBLICATIONS

U. Tietze et al.—Halbleiter–Schalungstechnik, 10 Auflage S. 469.**
D. Nührmann, "Das Grosse Werkbuch Elektronik", 6 Auflage, s. 2715–2716.**

* cited by examiner

Primary Examiner—Hezron Williams
Assistant Examiner—Rose M. Miller
(74) Attorney, Agent, or Firm—Kenyon & Kenyon

(57) ABSTRACT

An ultrasonic transmitter, particularly for an air bubble detector, having a transmitting stage and an ultrasonic crystal. The transmitting stage includes a multivibrator having a time-base circuit with two stable output states. A timing element is interconnected in the feedback loop of the time-base circuit. An ultrasonic crystal is interconnected with the feedback loop of the time-base circuit so that the electrical circuit oscillates at or near a resonance frequency of the ultrasonic crystal. The ultrasonic crystal may be disconnected so that the multivibrator oscillates automatically at its own natural frequency.

21 Claims, 3 Drawing Sheets

ULTRASONIC TRANSMITTER PARTICULARLY FOR AN AIR BUBBLE DETECTOR

FIELD OF THE INVENTION

The present invention relates to an ultrasonic transmitter, and in particular to an ultrasonic transmitter for an air bubble detector, having a transmitting stage and an ultrasonic crystal.

RELATED TECHNOLOGY

An ultrasonic crystal customarily comprises a piezoelectric element that is driven at one of its resonance frequencies. A problem is providing a transmitting stage that excites the ultrasonic crystal at precisely that resonance frequency whereby an output signal which is as strong as possible is generated in the ultrasonic crystal.

If the ultrasonic transmitter is put to use in an air bubble detector, then particular requirements pertaining to reliability must also be imposed on the ultrasonic transmitter. In an air bubble detector there is, between the ultrasonic transmitter and an appropriately arranged ultrasonic receiver, a tube that is to be monitored for air bubbles. When infusions are being administered to a patient, or when transfusions are being performed on a patient, the admission of air into the tubes used for these purposes must be detected, or the patient may face a life-threatening situation. In order to detect air bubbles in these cases, use is made of the fact that the attenuation of the ultrasonic transmission line changes as soon as an air bubble enters the tube located between the ultrasonic transmitter and the ultrasonic receiver.

U.S. Pat. No. 5,583,280 discloses an air bubble detector having a transmitting stage, comprising a frequency synthesizer that sweeps linearly within a frequency range, wherein a resonance frequency of the ultrasonic crystal also lies in this frequency range. As soon as the sweeping frequency synthesizer finds the resonance frequency of the ultrasonic crystal, the ultrasonic crystal is excited and the frequency synthesizer's sweep may start anew.

An air bubble detector having a transmitting stage that has a variable frequency synthesizer is described in European Patent Application No. 0 416 911 A2. A test circuit is also provided for identification of malfunctions.

European Patent Application No. 0 340 470 A1 describes an atomizer having an ultrasonic crystal and a voltage-controlled oscillator for excitation of the ultrasonic crystal. The oscillator is regulated by a delta generator so that its own frequency is periodically swept in a range that includes the series resonance of the ultrasonic crystal. By means of a superposed closed loop it is possible to lock in place the voltage-controlled oscillator onto the series resonance frequency of the ultrasonic crystal.

An atomizer having an ultrasonic crystal is also known from European Patent Application No. 0 084 485 A2. For excitation of the ultrasonic crystal a multivibrator and a pulse generator are interconnected in such a way that the pulse generator emits pulses to the ultrasonic crystal in beat with the multivibrator's natural frequency. The pulse has a system-excitation effect on the ultrasonic crystal, so that the ultrasonic crystal reacts to the pulse with a damped resonance vibration. Of course, with pulse operation there is the disadvantage that a pulse generator having an appropriate energy storage element is always required in order to provide the pulse energy, resulting in comparatively complex circuitry.

U.S. Pat. No. 5,583,280 describes a liquid-level indicator utilizing the ultrasonic principle and a feedback band-pass filter for excitation of the ultrasonic crystal. The filter locks onto the resonance frequency of the ultrasonic crystal, similar to the phase-locked loop device described above.

Prior ultrasonic transmitters have the disadvantage that the transmitting stages have relatively highly complex circuitry.

SUMMARY OF THE INVENTION

Accordingly, an object of the present invention is to provide an ultrasonic transmitter having a simply designed transmitting stage for excitation of a transmitting-end ultrasonic crystal which at the same time generates a strong output signal in the ultrasonic crystal.

The present invention provides an ultrasonic transmitter (20), particularly for an air bubble detector, having a transmitting stage (23) and having an ultrasonic crystal (5), the transmitting stage (23) having a multivibrator (22). The multivibrator (22) includes a time-base circuit (1) having two stable output states, and a timing element (2, 3) interconnected in the time-base circuit's feedback loop. The ultrasonic crystal (5) is interconnected with the time-base circuit's feedback loop in such a way that the transmitting stage (23) oscillates at or near a resonance frequency of said ultrasonic crystal, while, when said ultrasonic crystal is disconnected, the multivibrator (22) oscillates automatically at its own natural frequency.

According to the present invention, the transmitting stage has a multivibrator including a time-base circuit and a timing element interconnected in a feedback loop of the time-base circuit. The multivibrator starts oscillating almost automatically at its own natural frequency, which frequency is influenced essentially by the time-base circuit. According to the present invention, the ultrasonic crystal is interconnected with the feedback loop of the time-base circuit in such a way that the transmitting stage oscillates at or near a resonance frequency of the ultrasonic crystal. In contrast to prior excitation circuits, the ultrasonic crystal itself thereby functions as a frequency-determining component for a continuously generated transmission frequency. This makes the circuitry considerably less complex, and at the same time particularly insensitive to electromagnetic interference, which enhances reliability. In addition, the ultrasonic transmitter according to the present invention generates a very strong output signal, which in turn makes possible a simple design for the receiving circuit.

According to a preferred embodiment of the present invention, the timing element of the multivibrator comprises at least one RC element, and the ultrasonic crystal is connected in parallel to the resistance of an RC element. This ensures reliable buildup of oscillations in the circuit because the multivibrator will first start to oscillate at its own natural frequency and then will excite the ultrasonic crystal at a resonance frequency due to the abrupt level changes at the output of the time-base circuit.

According to another preferred embodiment of the present invention, a low-pass filter is provided at the output of the time-base circuit, in order to suppress buildup of oscillations of the ultrasonic crystal at the crystal's harmonics. In addition, selective buildup of oscillations can also be attained by having the transmitting stage oscillate below the appropriate resonance frequency of the ultrasonic crystal.

The ultrasonic crystal is driven at its lowest series resonance frequency. When dealing with a piezoelectric element for the ultrasonic crystal, the series resonance frequency will be largely independent of external influences, while the poorly defined electrode capacitance of the piezoelectric element will form the parallel resonance frequency.

According to another preferred embodiment of the present invention, the transmitting stage is interconnected logically with a test input, in order to activate or deactivate the ultrasonic transmitter for testing purposes. In this case the test input is interconnected with the input of the time-base circuit by means of an AND gate. In this way the ultrasonic transmitter can be tested for specific purposes for safety-engineering applications.

In another preferred embodiment of the present invention, the time-base circuit is a Schmitt trigger. A conventional Schmitt trigger is readily available as an integrated component and is barely loaded by a timing element in the feedback loop, permitting great leeway in choosing the components of the timing element.

An air bubble detector of the present invention includes an ultrasonic transmitter according to the present invention, an ultrasonic receiver and a tube inserted between the ultrasonic transmitter and the ultrasonic receiver.

BRIEF DESCRIPTION OF THE DRAWINGS

Additional details and advantages of the present invention are elucidated below with the aid of several embodiments represented in the drawings, in which.

DETAILED DESCRIPTION

Figure 1:
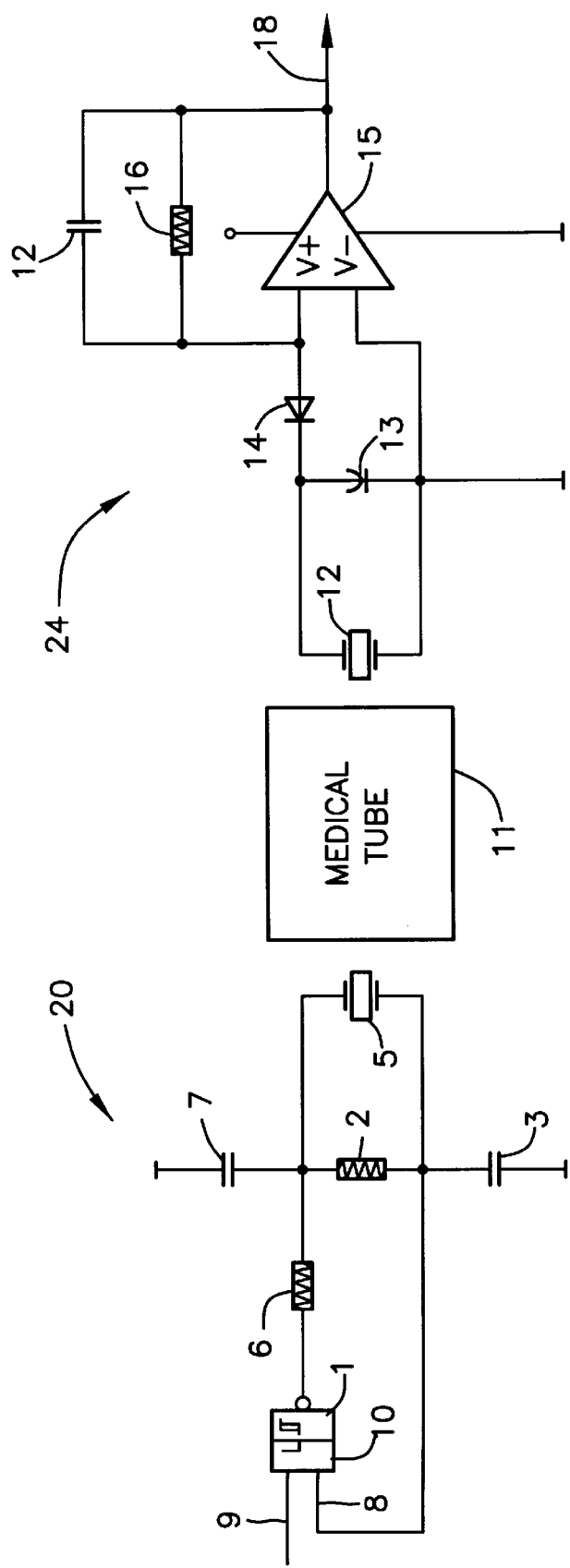
FIG. 1 shows an electrical circuit of an air bubble detector with an ultrasonic transmitter according to the present invention.
Figure 3:
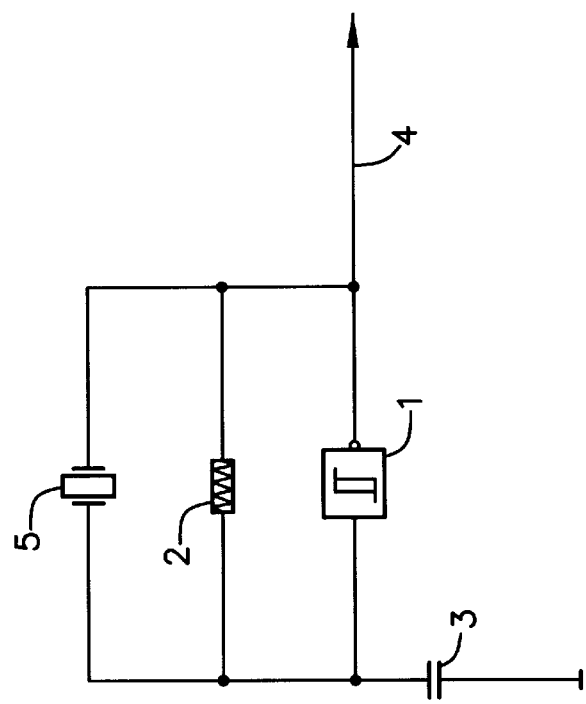
FIG. 3 shows an interconnection of an ultrasonic crystal with the feedback loop of the multivibrator shown in FIG. 2.
Figure 2:
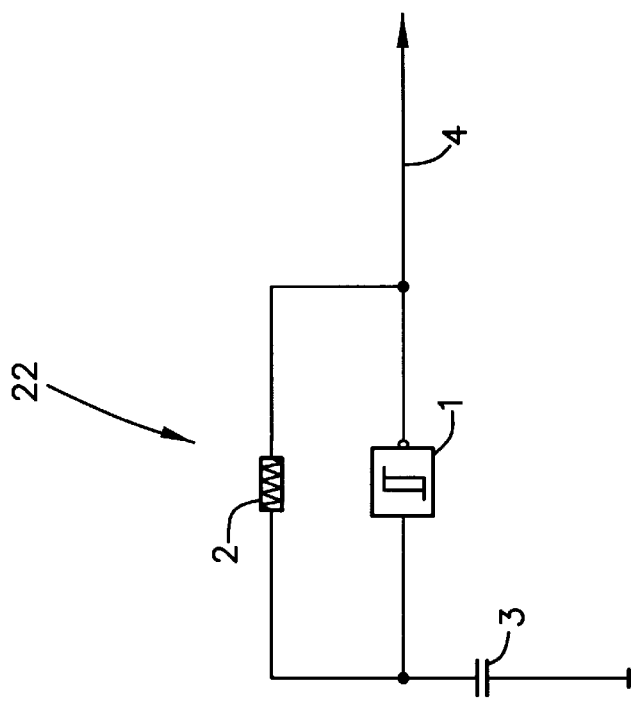
FIG. 2 shows a prior multivibrator.

Before describing the operation of the ultrasonic transmitter shown in FIG. 1, the principle of its operation may be elucidated with the aid of FIGS. 2 and 3. FIG. 2 shows the design of a prior multivibrator. Multivibrator 22 has as a time-base circuit Schmitt trigger 1, which is interconnected in its own feedback loop with resistance 2 and capacitance 3. Multivibrator 22 oscillates automatically at its own natural frequency, whereby capacitance 3 is charged via resistance 2 to the turn-off level of Schmitt trigger 1, and is then discharged again to the turn-on level of Schmitt trigger 1. Schmitt trigger 1 has at its own output two stable states, so that a periodic square-wave signal originates at output 4 of multivibrator 22.

FIG. 3 shows an interconnection of an ultrasonic crystal with the feedback loop of multivibrator 22 shown in FIG. 2. Here the ultrasonic crystal comprises piezoelectric element 5, wherein piezoelectric element 5 is connected in parallel to resistance 2. After being switched on, the circuit first starts oscillating at the multivibrator's natural frequency. Because of the square-wave signals at the output, piezoelectric element 5 will also be excited by square-wave signals, whereby a periodic signal having the resonance frequency of piezoelectric element 5 originates at the output of Schmitt trigger 1. In turn, square-wave signals having a frequency of the resonance frequency of piezoelectric element 5 are also generated at output 4, so that the circuit finally oscillates at the resonance frequency of piezoelectric element 5.

FIG. 1 shows an electrical circuit of an air bubble detector having an ultrasonic transmitter according to the present invention. The air bubble detector comprises ultrasonic transmitter 20, ultrasonic receiver 21, and medical tube 11 inserted between them, for detecting tube air bubbles reliably. Ultrasonic transmitter 20 differs from the circuit shown in FIG. 3 in that a low-pass filter comprising resistance 6 and capacitance 7 is provided at the output of Schmitt trigger 1, and the input of Schmitt trigger 1 is interconnected logically with test input 9. The low-pass filter comprising resistance 6 and capacitance 7 causes the ultrasonic crystal to start to oscillate reliably at its lowest resonance frequency, and causes the voltage across piezoelectric element 5 to be approximately sinusoidal. Test input 9 and feedback loop 8 are interconnected using AND gate 10. Schmitt trigger 1 can thereby be reliably activated or deactivated for purposes of testing. On the opposite side of medical tube 11 is ultrasonic receiver 21, which has piezoelectric element 12 of the same design as piezoelectric element 5. The voltage across piezoelectric element 12 is rectified using diodes 13 and 14 and smoothed via operational amplifier 15, and via resistance 16 and capacitance 17, so that the appropriate envelope signal is present at output 18. If an air bubble arrives in medical tube 11, then the attenuation in the ultrasonic transmission line between ultrasonic transmitter 20 and ultrasonic receiver 21 will change compared to when the tube is filled with liquid. The envelope signal at output 18 will thereby change, making detection of air bubbles inside medical tube 11 possible.

Figure 4:
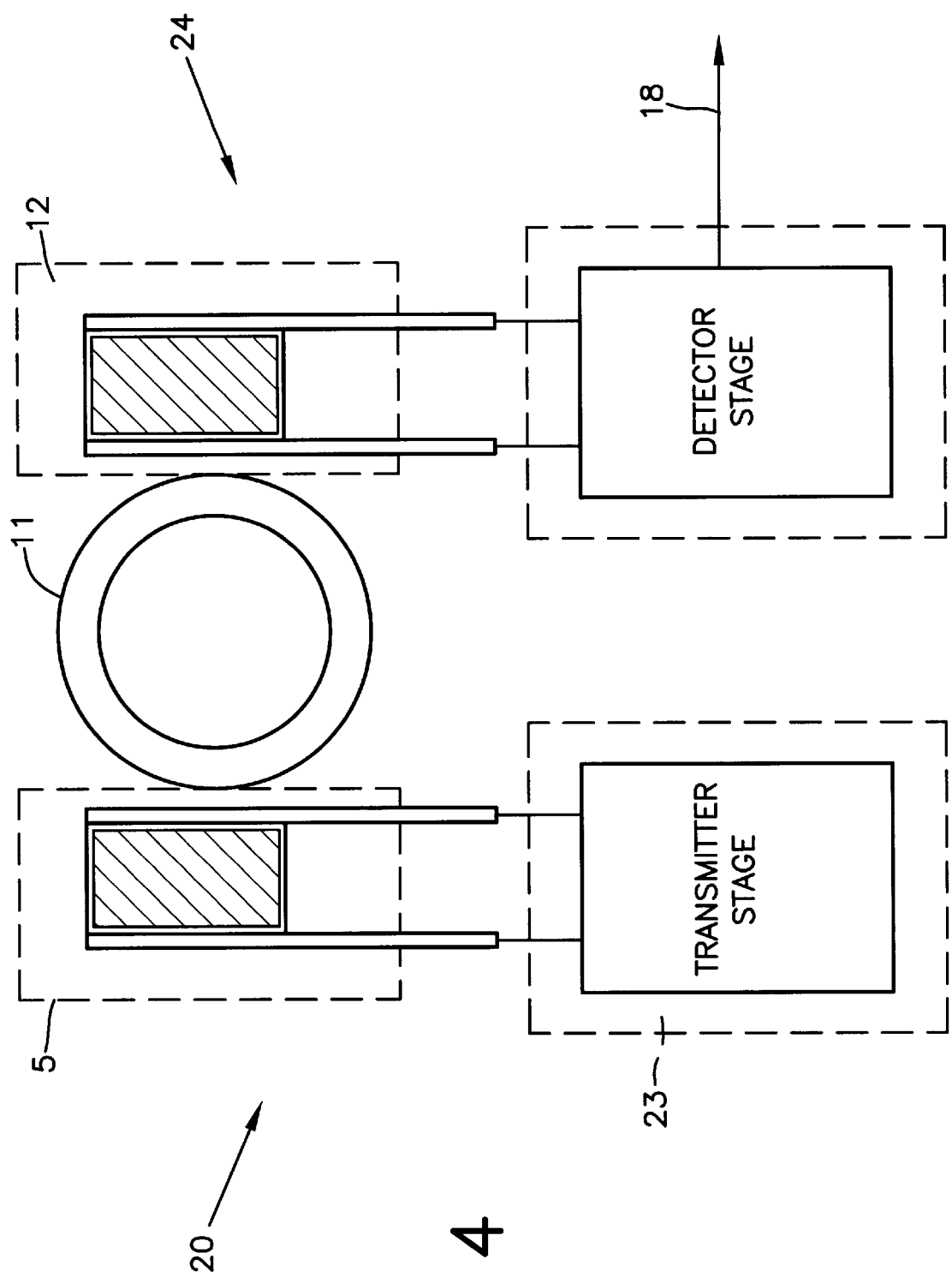
FIG. 4 shows a diagram of an air bubble detector according to the present invention.

FIG. 4 is a diagram of an air bubble detector of the electrical circuit shown in FIG. 1, having ultrasonic transmitter 20 and ultrasonic receiver 21. Ultrasonic crystals 5 and 12 essentially form a piezoelectric-vibrator plate having two means of connection. These means of connection are disposed at opposite sides of medical tube 11, which is to be monitored, so that the sound can travel from the transmitting-end ultrasonic crystal 5 to the receiving-end ultrasonic crystal 12. Because of necessary matching to the medical tube's acoustic impedance, the piezoelectric-vibrator plates are coupled to the medical tube using a coupling medium suited for this purpose. For this reason, and for physical protection, the ultrasonic crystals are incorporated integrally into a housing that at the same time constitutes an appropriate storage place for the tube to be monitored. The transmitting-end ultrasonic crystal 5 is triggered by transmitting stage 23 in such a way that ultrasonic crystal 5 oscillates at its own lowest resonance frequency. The receiving-end ultrasonic crystal 12 has the same design as the transmitting-end ultrasonic crystal, so that its greatest responsiveness is at the transmission frequency of ultrasonic transmitter 20. An output signal 18, which is as strong as possible and easy to utilize, is thereby obtained at ultrasonic receiver 21.

What is claimed is:

1. An ultrasonic transmitter comprising:
  a transmitting stage including a multivibrator, the multivibrator including a time-base circuit having two stable output states and a timing element interconnected in a feedback loop of the time-base circuit; and
  an ultrasonic crystal interconnected with the feedback loop of the time-base circuit so that the transmitting stage oscillates at or near a resonance frequency of the ultrasonic crystal, the multivibrator oscillating at a multivibrator natural frequency when the ultrasonic crystal is disconnected from the feedback loop of the time-base circuit.

2. The ultrasonic transmitter recited in claim 1 wherein the ultrasonic transmitter is included in an air bubble detector.

3. The ultrasonic transmitter recited in claim 1 wherein the timing element includes at least one RC element including a resistor and a capacitor.

4. The ultrasonic transmitter recited in claim 3 wherein the ultrasonic crystal is connected in parallel to the resistor.

5. The ultrasonic transmitter recited in claim 1 wherein the time-base circuit further includes an output, and further comprising a low-pass filter at the output for suppressing buildup of oscillations of the ultrasonic crystal.

6. The ultrasonic transmitter recited in claim 5 wherein the ultrasonic crystal is driven at a lowest series resonance frequency.

7. The ultrasonic transmitter as recited in claim 1 wherein the transmitting stage oscillates below a resonance frequency of the ultrasonic crystal.

8. The ultrasonic transmitter as recited in claim 1 further comprising a test input logically interconnected with the transmitting stage for activating and deactivating the ultrasonic transmitter for testing purposes.

9. The ultrasonic transmitter as recited in claim 8 wherein the time-base circuit further includes an input, and further comprising an AND gate interconnecting the test input with the input of the time-base circuit.

10. The ultrasonic transmitter as recited in claim 1 wherein the ultrasonic crystal is a piezoelectric element.

11. The ultrasonic transmitter as recited in claim 1 wherein the time-base circuit is a Schmitt trigger.

12. An air bubble detector comprising:

an ultrasonic transmitter including:

a transmitting stage including a multivibrator, the multivibrator including a time-base circuit having two stable output states and a timing element interconnected in a feedback loop of the time-base circuit; and an ultrasonic crystal interconnected with the feedback loop of the time-base circuit so that the transmitting stage oscillating at or near a resonance frequency of the ultrasonic crystal, the multivibrator oscillating at a multivibrator natural frequency when the ultrasonic crystal is disconnected from the feedback loop of the time-base circuit;

an ultrasonic receiver; and a tube disposed between the ultrasonic transmitter and the ultrasonic receiver.

13. The air bubble detector recited in claim 12 wherein the timing element includes at least one RC element including a resistor and a capacitor.

14. The air bubble detector recited in claim 13 wherein the ultrasonic crystal is connected in parallel to the resistor.

15. The air bubble detector recited in claim 12 wherein the time-base circuit further includes an output, and further comprising a low-pass filter at the output of the time-base circuit for suppressing buildup of oscillations of the ultrasonic crystal.

16. The air bubble detector recited in claim 15 wherein the ultrasonic crystal is driven at a lowest series resonance frequency.

17. The air bubble detector as recited in claim 12 wherein the transmitting stage oscillates below a resonance frequency of the ultrasonic crystal.

18. The air bubble detector as recited in claim 12 further comprising a test input logically interconnected with the transmitting stage for activating and deactivating the ultrasonic transmitter for testing purposes.

19. The air bubble detector as recited in claim 18 wherein the time-base circuit further includes an input, and further comprising an AND gate interconnecting the test input with the input of the time-base circuit.

20. The air bubble detector as recited in claim 12 wherein the ultrasonic crystal is a piezoelectric element.

21. The air bubble detector as recited in claim 12 wherein the time-base circuit is a Schmitt trigger.

* * * * *